US00PP27826P2

(12) United States Plant Patent
Zaiger et al.

(10) Patent No.: US PP27,826 P2
(45) Date of Patent: Apr. 4, 2017

(54) INTERSPECIFIC TREE NAMED 'BELLA JEAN'

(50) Latin Name: **Interspecific *Prunus* species**
Varietal Denomination: Bella Jean

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 14/998,480

(22) Filed: Jan. 12, 2016

(51) Int. Cl.
*A01H 5/00* (2006.01)

(52) U.S. Cl.
USPC ..... Plt./180

(58) Field of Classification Search
USPC ..... Plt./180
See application file for complete search history.

*Primary Examiner* — Annette Para

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of large size, yellow flesh fruit.
3. Fruit with very good flavor and eating quality.
4. Fruit with an attractive red skin color.
5. Fruit with a high degree of soluble solids (Brix) of 18.2°.

1 Drawing Sheet

Botanical designation: Interspecific *Prunus* species.
Variety denomination: 'Bella Jean'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

Prior Varieties

Among the existing varieties of interspecific trees, which are known to us, and mentioned herein, 'Bella Gold' Interspecific (U.S. Plant Pat. No. 17,826), 'Coparose' Interspecific (U.S. Plant Pat. No. 20,173) and the proprietary non-patented interspecific varieties '300LP494', '146LH30' and '332LH358'.

STATEMENT REGARDING FEDERALLY SPONSORED RESEARCH AND DEVELOPMENT

Not applicable.

ORIGIN OF THE VARIETY

The new variety of interspecific tree was originated by us from crosses between *Prunus salicina, Prunus armeniaca* and *Prunus persica* var. *nucipersica* in our experimental orchard located near Modesto, Calif. as a first generation cross between our non-patented proprietary interspecific seedling '300LP494' and 'Bella Gold' Interspecific (U.S. Plant Pat. No. 17,826). The seed parent (300LP494) is a first generation cross from our proprietary non-patented interspecific seedling '146LH30' and our proprietary non-patented interspecific genetic dwarf nectarine '332LH358'. A large number of these first generation seedlings were budded onto older established trees of 'Nemaguard' Rootstock (non-patented) to enhance earlier fruit production. Under close and careful observation the present budded seedling exhibited desirable fruit and tree characteristics and was selected in 2007 for additional asexual propagation and commercialization.

ASEXUAL REPRODUCTION OF THE VARIETY

In 2007 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree which consists of Plum, Apricot and Nectarine has vigorous, upright growth and is a regular and productive bearer of large size fruit with attractive red skin color. The fruit is further characterized by its firm, yellow flesh and very good flavor and eating quality. In comparison to its proprietary non-patented interspecific seed parent (300LP494) the fruit of the new variety is approximately 47 days earlier in maturity and has red skin compared to yellow-orange skin. In comparison to its pollen parent 'Bella Gold' Interspecific (U.S. Plant Pat. No. 17,826) the fruit of the new variety is larger in size, has red skin compared to bicolor (yellow and red skin) and is approximately 21 days later in maturity. In comparison to the commercial variety 'Coparose' Interspecific (U.S. Plant Pat. No. 20,173) the fruit of the new variety is larger in size, has pubescent skin compared to glabrous and is approximately 5 days later in maturity.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from an 8 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 8 year old specimens grown near Modesto, Calif., with color in accordance with Munsell Book of Color published in 1958.

Tree:

*Size*.—Large, usually pruned to 3 to 3.5 meters in height and width for economical harvesting of fruit. Varies with different cultural practices.

*Vigor*.—Vigorous, tree growth of approximately 1.5 to 2 meters in height the first growing season. Varies with cultural practices, soil type, fertility of soil and climatic conditions.

*Form*.—Upright, usually pruned to vase shape.

*Branching habit*.—Upright, crotch angle approximately 30°, increases with heavy crop load.

*Productivity*.—Productive, thinning and spacing of fruit necessary for desired market size. Fruit set varies with climatic conditions during bloom time.

*Bearer*.—Regular, adequate fruit set 6 consecutive years. No alternate bearing observed.

*Fertility*.—Self-sterile, pollinator required.

*Density*.—Medium dense, usually pruned to vase shape to increase air movement and sunlight to center of tree to enhance fruit color and health of fruit spurs.

*Hardiness*.—Hardy in all stone fruit growing areas of California. Tree grown in USDA Hardiness Zone 9. Winter chilling requirement approximately 700 hours at or below 45° F.

Trunk:

*Size*.—Medium. Average circumference 50.8 cm at 25.4 cm above ground on a 8 year old tree.

*Stocky*.—Medium stocky.

*Texture*.—Medium shaggy, roughness increases with age.

*Color*.—Varies from 10YR 4/2 to 2.5Y 4/2.

Branches:

*Size*.—Medium. Average circumference 11.2 cm at 1.2 meters above ground on a 8 year old tree. Crotch angle approximately 30°, increases with heavy crop load.

*Surface texture*.—New growth relatively smooth. Mature growth medium rough, roughness increases with age.

*Lenticels*.—Average number 59 in a 25.8 square cm area. Average length 3.9 mm. Average width 1.7 mm. Color varies from 7.5YR 4/6 to 7.5YR 4/8.

*Color*.—New growth varies from 5GY 6/6 to 5GY 5/6. Mature growth varies from 7.5YR 3/2 to 10YR 3/4, varies with age of growth.

Leaves:

*Size*.—Large. Average length 138.5 mm. Average width 67.7 mm.

*Form*.—Obovate.

*Apex*.—Acuminate.

*Base*.—Cuneate.

*Margin*.—Crenate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Small. Average length 11.9 mm. Average width 1.9 mm. Surface — pubescent. Longitudinally grooved. Color varies from 5GY 4/8 to 5GY 5/8.

*Glands*.—Type — globose. Size — medium to large. Average length 1.1 mm. Average diameter 0.8 mm. Located primarily on the base of the leaf blade and the upper portion of the petiole. Color varies from 5YR 4/6 to 5YR 3/6.

*Stipules*.—None present at time of measurement.

*Color*.—Upper surface varies from 5GY 3/4 to 5GY 3/6. Lower surface varies from 5GY 4/4 to 2.5GY 5/4. Midvein color varies from 10Y 8/4 to 2.5GY 7/4.

Flower buds:

*Size*.—Medium. Average length 9.0 mm. Average diameter 6.0 mm.

*Hardiness*.—Hardy in all stone fruit growing areas of California.

*Density*.—Medium dense.

*Form*.—Conical, becoming elongated just before opening.

*Pedicel*.—Average length 6.7 mm. Average width 0.7 mm. Surface — glabrous. Color varies from 2.5GY 6/8 to 5GY 7/8.

*Color*.—N 9.5/(white).

*Number of buds per spur*.—Varies from 4 to 10, average number 7.

Flowers:

*Blooming period*.—Date of First Bloom Mar. 1, 2015. Date of Petal Fall Mar. 11, 2015, varies slightly with climatic conditions.

*Size*.—Medium. Average height 9.5 mm. Average diameter 18.6 mm.

*Petals*.—Normally 5, alternately arranged to sepals. Size — medium. Average length 10.3 mm. Average width 6.6 mm. Petal apex — rounded. Petal base — truncate. Form — elliptical to globose. Arrangement — free. Margin — sinuate. Color N 9.5/(white). Both upper and lower surfaces glabrous.

*Sepals*.—Normally 5, alternately arranged to petals. Size — small to medium. Average length 3.5 mm. Average width 2.4 mm. Shape — triangular. Apex — ovate to triangular. Margin — entire. Both upper and lower surfaces glabrous. Color — upper surface varies from 5GY 6/8 to 5GY 7/4. Lower surface varies from 5GY 5/8 to 2.5GY 6/10.

*Stamens*.—Average number per flower 33. Average filament length 7.9 mm. On average the stamens are above the height of the petals. Filament color N 9.5/(white). Anther color varies from 2.5Y 7/8 to 5Y 8/8.

*Pollen*.—Self-sterile, pollinator required. Color varies from 2.5Y 7/10 to 5Y 7/10.

*Pistil*.—Number — normally one. Surface — pubescent. Average length 9.2 mm. Position of stigma even with anthers. Color varies from 2.5GY 8/6 to 2.5GY 7/6.

*Fragrance*.—Heavy aroma.

*Color*.—N 9.5/(white).

*Pedicel*.—Average length 7.3 mm. Average width 0.8 mm. Color 2.5GY 6/8.

*Number flowers per flower bud*.—Average number 3, varies from 2 to 4.

Fruit:

*Maturity when described*.—Firm ripe and ready for consumption.

*Date of first picking*.—Jul. 6, 2015.

*Date of last picking*.—Jul. 16, 2015, varies slightly with climatic conditions.

*Size*.—Large. Average diameter axially 59.6 mm. Average transversely in suture plane 65.3 mm. Average weight 164.7 grams, varies slightly with fertility of the soil, amount of thinning and climatic conditions.

*Form*.—Globose.

*Suture*.—Some fruit with slight suture, extends from base to apex.

*Ventral surface*.—Nearly smooth.

*Apex*.—Rounded.

*Base*.—Retuse.

*Stem cavity*.—Rounded to slightly elongated in suture plane. Average depth 4.1 mm. Average diameter 4.8 mm.

Stem:

*Size*.—Small to medium. Average length 9.6 mm. Average diameter 2.0 mm.

*Color*.—Varies from 10Y 6/6 to 5YR 3/6.

Flesh:

*Ripens*.—Evenly.

*Texture*.—Firm, meaty.

*Fibers*.—Few, small, tender.

*Firmness*.—Firm, comparable to other commercial interspecific varieties.

*Aroma*.—Very slight.

*Amydgalin*.—Undetected.

*Eating quality*.—Very good.

*Flavor*.—Very good, good balance between acid and sugar.

*Juice*.—Heavy amount, enhances flavor.

*Acidity*.—Not available.

*Brix*.—Average Brix 18.2°, varies slightly with amount of fruit per tree and climatic conditions.

*Color*.—Varies from 10YR 7/8 to 7.5R 4/10.

*Pit cavity*.—Average length 29.0 mm. Average width 20.1 mm. Average depth 6.2 mm. Color varies from 7.5YR 4/12 to 10R 5/12.

Skin:

*Thickness*.—Medium.

*Surface*.—Smooth.

*Pubescence*.—Moderate amount, very short in length.

*Tendency to crack*.—None.

*Color*.—Ground color varies from 10YR 6/8 to 7.5YR 6/10. Overspread with 7.5R 3/6 to 7.5R 3/8.

*Tenacity*.—Tenacious to the flesh.

*Astringency*.—Slight to none.

Stone:

*Type*.—Clingstone, medium adherence to flesh.

*Size*.—Medium. Average length 28.0 mm. Average width 19.1 mm. Average thickness 10.4 mm.

*Form*.—Ovoid.

*Base*.—Flat.

*Apex*.—Pointed. Average length 1.7 mm.

*Surface*.—Slightly pitted throughout.

*Sides*.—Unequal, one side extending further from suture plane.

*Ridges*.—Very narrow, small ridge near groove on each side of suture, extends from base to apex.

*Tendency to split*.—None.

*Color*.—Varies from 7.5YR 7/6 to 7.5YR 6/8 when dry.

Kernel:

*Size*.—Small to medium. Average length 14.3 mm. Average width 9.8 mm. Average depth 4.4 mm.

*Form*.—Ovoid.

*Viability*.—Viable, complete embryo development.

*Skin color*.—Varies from 2.5Y 8/6 to 2.5Y 8.5/6.

Use: Dessert.

*Market*.—Local and long distance.

Keeping quality: Good, held firm in cold storage for 3 weeks at 38° to 42° F. without internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices.

The present new variety of interspecific tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

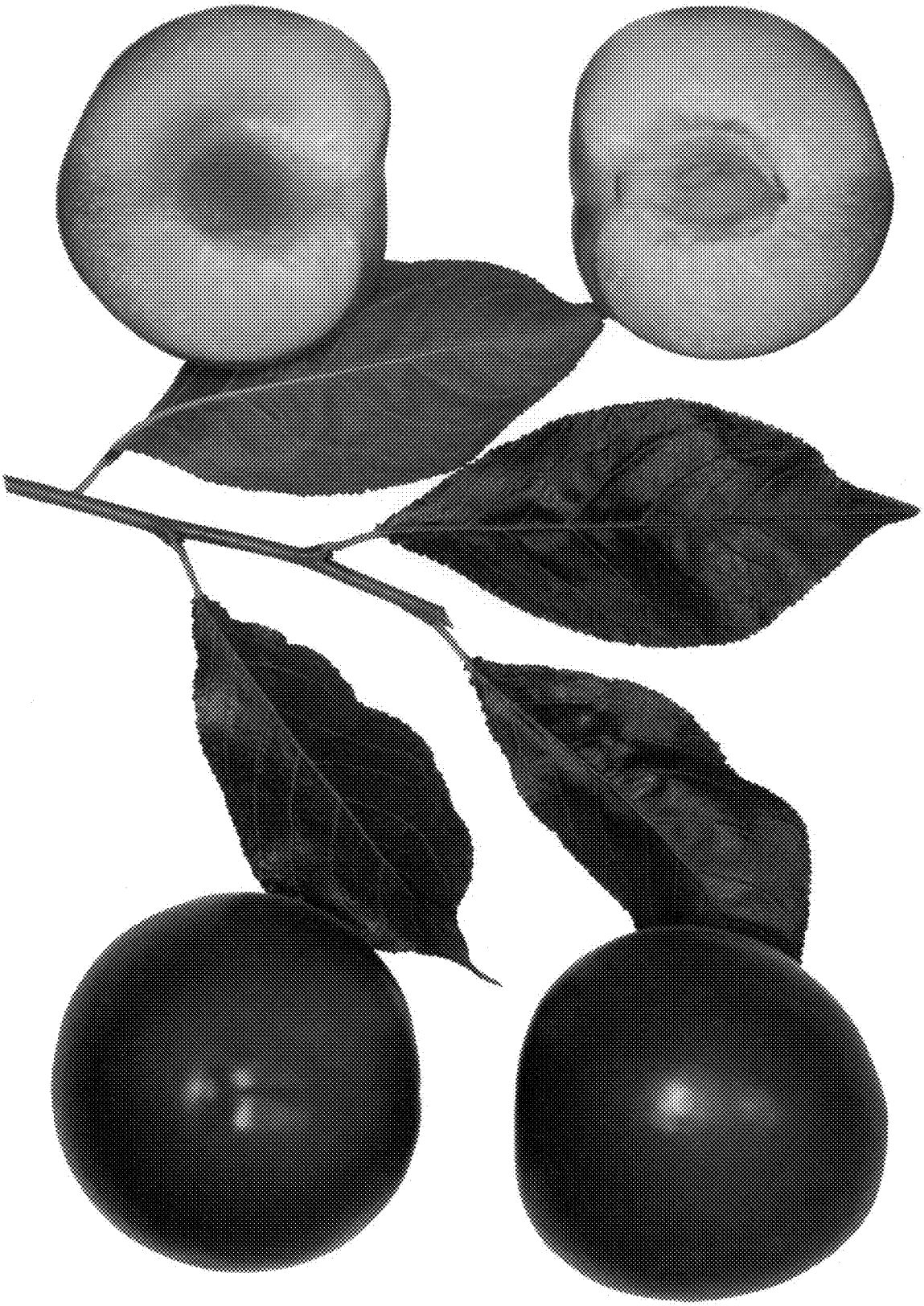

* * * * *